United States Patent [19]

Ventimiglia et al.

[11] Patent Number: 5,337,290

[45] Date of Patent: Aug. 9, 1994

[54] HEALTH WATCH

[76] Inventors: Phillip Ventimiglia, 40 Lakeview Dr., Cherry Hill, N.J. 08003; Louis E. Sansone, 286 Woodward Rd., Brooklyn, Conn. 06234

[21] Appl. No.: 829,428

[22] Filed: Feb. 3, 1992

[51] Int. Cl.$^5$ .................. G04B 47/00; G07F 11/00
[52] U.S. Cl. ............................ 368/10; 368/82; 221/2; 364/413.02
[58] Field of Search ............... 368/10, 82, 84; 221/2, 221/3, 15

[56] References Cited

U.S. PATENT DOCUMENTS

| | | | |
|---|---|---|---|
| 4,748,600 | 5/1988 | Urquhart | 368/10 |
| 5,012,229 | 4/1991 | Lennon et al. | 368/10 |

Primary Examiner—Vit W. Miska
Attorney, Agent, or Firm—Michael I. Kroll

[57] ABSTRACT

A Health-Watch that provides nearly instant access to critical medical data. It is worn on the wrist like a conventional wrist watch and contains two levels of data. The first level, which contains the most critical medical data, can be displayed on the watch's alphanumeric display screen. The second level of data, which is of lower priority and is frequently more detailed, can be accessed by an external data terminal via a serial data port on the Health-Watch. The Health-Watch combines all circuitry including memory onto a single Application Specific Integrated Circuit. An UPDATE mode provides for updating medical data.

1 Claim, 2 Drawing Sheets

HEALTH WATCH

BACKGROUND OF THE INVENTION

The instant invention relates, generally, to the field of data storage and display, and, more specifically, to the field of portable medical information storage and display.

In emergency medical situations, providing health and personal information rapidly to medical services can be a life or death issue. The patient may be unconscious and not be able to provide information, or, even if conscious, the patient may be incapable of providing necessary information.

A number of portable electronic data storage and retrieval systems have already been proposed to address this need. These include the use of data stored on a smart card or on an optical disk. The smart card stores data in a business-card sized format in solid state memory contained within the card. The optical disk stores data that must be retrieved optically by a scanning laser. Both the smart card and the optical disk require the use of a reader and a computer, otherwise they are useless. An Emergency Medical Technician at the scene of an accident would not be able to gain access to any of the information on a smart card or optical disk. That information could mean the difference between life and death.

Another disadvantage of smart cards and optical disks is the lack of standards. Presently, there are at least sixty different standards of smart cards and many of optical disks. In many instances the reader a hospital has could be incompatible with the patient's smart card or optical disk.

There is another inherent problem with achieving a wide distribution of smart card and optical disk technology. It is difficult to convince a hospital or doctor to buy an expensive reader if nobody already uses smart card or optical disk media. Conversely, it is difficult to convince a consumer to but a smart card or optical disk if they are useless because hospitals and doctors do not have a reader.

SUMMARY OF THE INVENTION

It is, therefore, a primary object of the present invention is to provide a Health-Watch that allows the consumer to have access to its information immediately.

Another primary object is to provide a Health-Watch that is operable even if the doctor or hospital does not have the software, hardware, or interconnect cables needed to link it to the hospital computer.

Another object is to provide a Health-Watch provides two levels of data. At the first level, which contains the most frequently needed and highest priority data, the data can be displayed on the Health-Watch's built-in screen. The second level data, which is of lower priority and contains greater detail, can be accessed by an external data terminal via a built-in serial interface.

Another object is to provide a Health-Watch that allows the user to choose from among a number of first level display modes including: time, date, vital signs, chronic conditions, allergies, medications and personal data.

Yet another object is to provide a Health-Watch that allows a data terminal accessing the Health-Watch to choose from among a number of second level data sets including: family history, history of illnesses, immunization history, history of major operations, and the results of previous major tests.

Yet another object is to provide a Health-Watch that is simple to operate and inexpensive to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows.

LIST OF COMPONENTS

Figure 1:
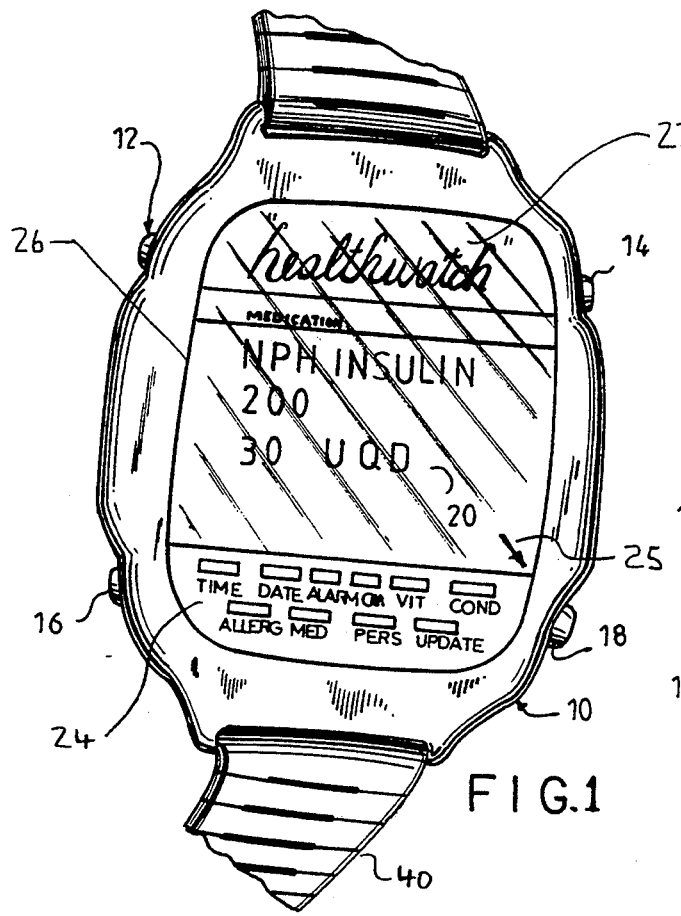
FIG. 1 is an enlarged partial perspective view of the invention illustrated while operating in the "MEDICATION" mode. Other modes include: TIME, DATE, ALARM, CHRONOGRAPH, VITAL SIGNS, CHRONIC CONDITIONS, ALLERGIES, PERSONAL, and UPDATE.
Figure 2:
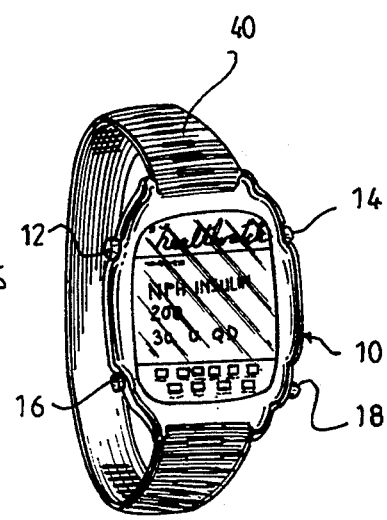
FIG. 2 is a perspective view of the entire invention.
Figure 3A:
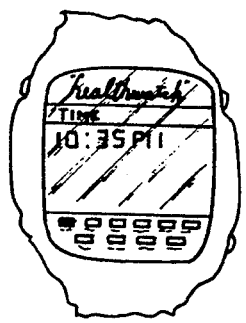
FIG. 3A to 3G are illustrations of typical screens displayed for each of the operating modes (except ALARM, CHRONOGRAPH, and UPDATE): A) TIME, B) DATE, C) VITAL SIGNS, D) CHRONIC CONDITIONS, E) ALLERGIES, F) MEDICATION, and F) PERSONAL.
Figure 3B:
Figure 3C:
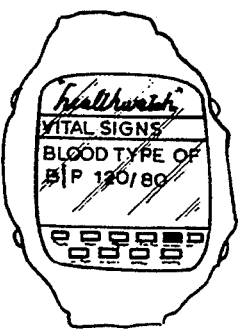
Figure 3D:
Figure 3E:
Figure 3F:
Figure 3G:
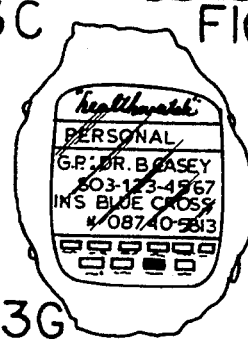

| DRAWING REFERENCE | DESCRIPTION |
| --- | --- |
| 10 | WATCH CASE |
| 12 | TIME/DATE SET BUTTON |
| 14 | ALARM/CHRONOGRAPH SET BUTTON |
| 16 | MODE SET BUTTON |
| 18 | LAP/CONTINUE BUTTON |
| 20 | ALPHANUMERIC DISPLAY AREA |
| 22 | HEALTH-WATCH LOGO |
| 24 | MODE DISPLAY AREA |
| 26 | ALPHANUMERIC LCD DISPLAY SCREEN |
| 28 | 8051-BASED ASIC |
| 28A | LCD DISPLAY DRIVER |
| 28B | 8051 CPU I/O CONTROLLER |
| 28C | PROGRAM ROM |
| 28D | EEPROM OR BATTERY-BACKED SRAM |
| 28E | SERIAL PORT |
| 28F | CLOCK CIRCUIT |
| 30 | COMPUTER INTERFACE |
| 32 | STEREO MINI-PHONO PLUG |
| 34 | TWO CONDUCTOR CABLE |
| 36 | RS-232-ADAPTER |
| 38 | PIEZO TRANSDUCER |
| 40 | WATCH BAND |

DETAILED DESCRIPTION OF THE PREFERRED EMBODIMENTS

The Health-Watch 10 appears much like a conventional wrist watch and has the same form factor. It may be worn as a wrist watch with band 40, or it may be worn as a pendant watch, or a pocket watch, or in any convenient manner.

The Health-Watch displays both conventional and health-related information on alphanumeric display screen 26. This may be an LCD display, an LED display, a gas plasma display, an electro-luminescent display, or any other type.

This embodiment of the Health-Watch has four operating buttons. The TIE/DATE set button 12 is used to set the time and the date in a manner similar to a conventional watch. The ALARM/CHRONOGRAPH set button 14 is used to set the alarm and chronograph functions in a manner similar to a conventional watch. The watch may contain a number of alarms; i.e. 1, 2, 5, etc. The MODE SET button 16 is used to switch between display modes which include: TIME, DATE, ALARM, CHRONOGRAPH, VITAL SIGNS, CHRONIC CONDITIONS, ALLERGIES, MEDICATIONS, PERSONAL INFORMATION, and UPDATE. The LAP/CONTINUE BUTTON 18 has two functions. It is used to time laps when the Health-Watch is used as a chronograph and the CONTINUE function is used to scroll to the next screen if there is more data to display than will fit on a single screen. If there is more data the arrow 25 will be displayed. At the end of the data the arrow 25 is replaced by the word END.

The alphanumeric screen 26 has three display regions. In region 20 the alphanumeric data is displayed. In region 22 the logo is displayed. In region 24 the active mode is highlighted by darkening the appropriate rectangle. Examples of each of the major modes of display are illustrated in FIGS. 3A to 3G. If the Health-Watch is left in any medical display mode for more than some pre-determined period of time, the display automatically returns to the TIME mode.

Figure 4:
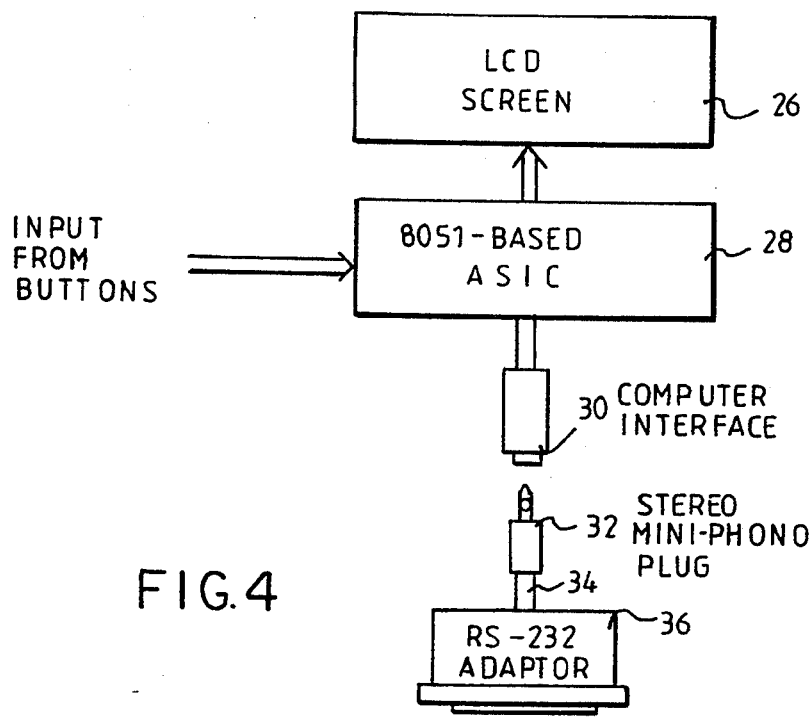
FIG. 4 is an electronic block diagram of the invention.
Figure 5:
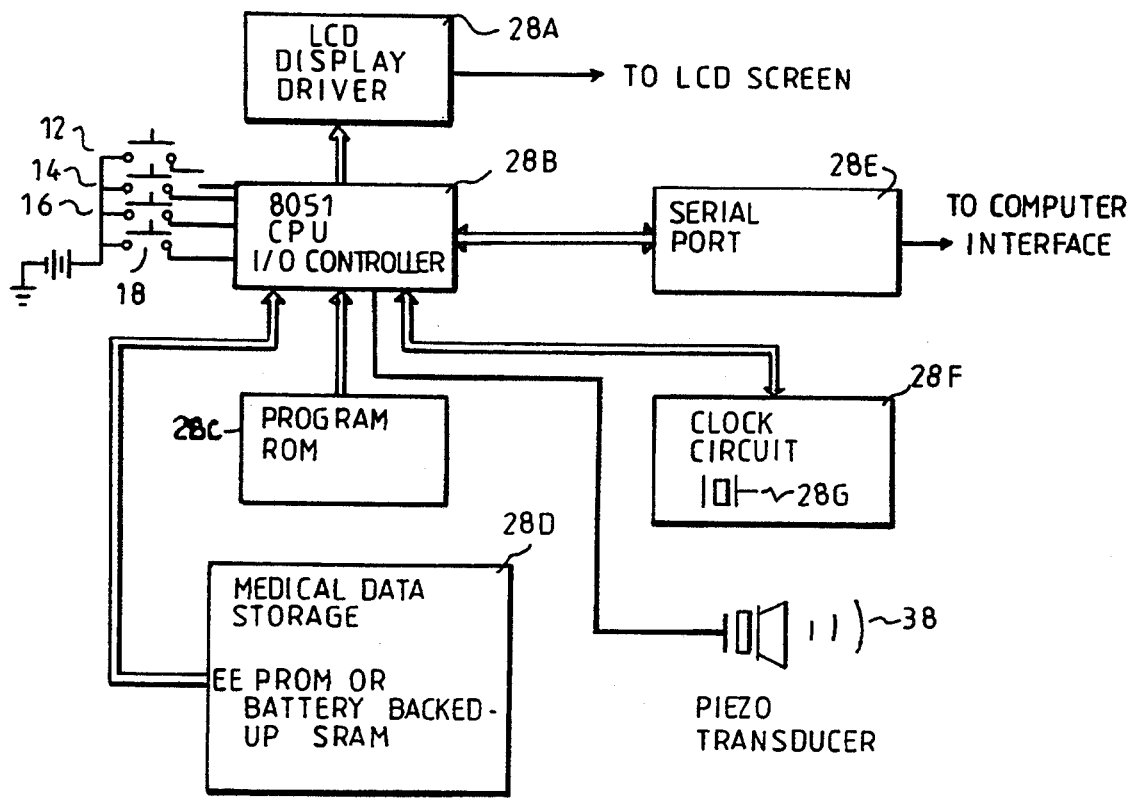
FIG. 5 is an electronic block diagram of the 8051-based Application Specific Integrated Circuit, ASIC, portion of the invention.

The detailed operation of the Health-Watch may best be understood with reference to FIGS. 4 and 5. The electronic circuitry for the Health-Watch is contained with one application specific integrated circuit 28. This may be a gate array or a standard cell or a compiled cell device. This ASIC contains a core microprocessor, such as an Intel 8051 or a Dallas Semiconductor DS5000. The 8051 core processor is combined with the input/output controller in block 28B. The output of CPU 28B is displayed on LCD screen 26 via the LCD display driver 28A. The operating program for the CPU is contained in program ROM 28C. The medical data needs to be stored in safe non-volatile form. The nonvolatile medical data storage 28D may be in the form of an electrical erasable programmable read only memory (EEPROM) or a static random access memory (SRAM) backed up by a battery. Clock circuit 28G is used to operate CPU 28B and serves as a reference to synchronize all other circuits.

The Health-Watch is designed to have its second level of data accessed by an external data terminal. This data may include: family history, history of illness, immunization history, history of major operations, results of previous major tests, etc. The ASIC 28 contains a serial port 28E that converts data stored in parallel form into serial form. This serial data may be transmitted via a pair of conductors. The output of the serial port 28E transmits a bidirectional data stream to computer interface 30. A stereo mini-phono plug 32 plugs into computer interface 30. The serial data stream is transmitted via two conductor cable 34. In order to affect an interface to an existing data terminal or personal computer, an RS-232 adapter is provided.

When the Health-Watch is in UPDATE mode, data from the external data terminal may be input to the Health-Watch. This is the technique for updating the information stored in the non-volatile memory 28D.

In order to sound the audible alarms and other watch- and chronograph-related sounds, a piezo transducer 38 is provided.

While certain novel features of this invention have been shown and described and are pointed out in the annexed claims, it will be understood that various omissions, substitutions and changes in the forms and the details of the device illustrated and in its operation can be made by those skilled in the art without departing from the spirit of the invention.

What is claimed is:
1. A Health-Watch comprising:
   a. a watch case;
   b. an alphanumeric screen disposed on said watch case, displays both conventional and health-related information on said alphanumeric display screen, a first level of data sets is displayed on said alphanumeric screen and a second level of data sets is transmitted to an external data terminal via a data interface, said first level of data comprises high priority medical information and said second level comprises lower priority, one of the first level of data sets comprises medications currently being taken, one of the first level of data sets comprises a list of chronic conditions, one of the first level of data sets comprises a list of vital signs, one of the first level of data sets comprises a list of allergies, one of the first level of data sets comprises personal information, one of the first level of data sets comprises the time, one of the first level of data sets comprises the date, one of the first level of data sets comprises alarm settings, one of the first level of data sets comprises chronograph information, said alphanumeric screen further comprises a region which displays headings for each of said first level of data sets such that when one data set is displayed, or about to be displayed, the heading corresponding to that data set is highlighted, said alphanumeric screen further comprises an indicator that displays one indication if the information on said screen is complete and displays another indication if said data continues thereby allowing a user to scroll to the next screen, said alphanumeric screen has three display regions, they are alphanumeric data, logo and the active mode, fi the Health-Watch is left in any medical display mode for more than some pre-determined period of time, the display automatically returns to the display of time,
   c. electronic circuitry for timing, alarm, data storage, data retrieval, data interface, and data display, disposed within said watch case and contains an Application Integrated circuit including a central processing unit and an Input/Output controller connected to said central processing unit, a display driver that takes data from said central processing unit and converts it into the electrical signals required by said alphanumeric display, a program read only memory ROM connected to said central processing unit, wherein said ROM contains the operating program for the Health-Watch, a nonvolatile memory connected to said central processing unit wherein said non-volatile memory contains said data sets, a clock circuit connected to said CPU, and a serial port connected to said central processing unit such that data in serial format can be input or output from said port using only two conductors so that Health-Watch can be controlled or accessed by an accessory data terminal, one of the second level of data sets comprises family history, one of the second level of data sets comprises history of illnesses, one of the second level of data sets comprises immunization history, one of the second level of data sets comprises operations, one of the second level of data sets comprises results of tests, d. a MODE button that allows a user to select the mode of data to be displayed and a LAP/CONTINUE button that allows a user to scroll between two display screens, the LAP function is used to time laps when the Health watch is used as a chronograph and the CONTINUE function is used to scroll the next screen if there is more data to display than will fit on a single screen;

e. a transducer that converts said electrical signals into sound for audible alarms; and f. a computer interface, connected to the output of said serial port, a two conductor plug that can be inserted into said computer interface, a two conductor cable, and an adaptor on the end of said two conductor cable, such that said adaptor may be plugged into an accessory computer, said adaptor conforms to the RS-232 protocol.

* * * * *